United States Patent [19]
Lee

[11] 3,975,824
[45] Aug. 24, 1976

[54] ORTHODONTIC BRACKETS

[76] Inventor: Brian William Lee, 526 Riverdale Road, Camberwell, Victoria, Australia

[22] Filed: Mar. 28, 1975

[21] Appl. No.: 562,917

[30] Foreign Application Priority Data
Apr. 2, 1974 Australia.............................. 7126/74

[52] U.S. Cl................................................ 32/14 A
[51] Int. Cl.²......................................... A61C 7/00
[58] Field of Search ................................... 32/14 A

[56] References Cited
UNITED STATES PATENTS

| | | | |
|---|---|---|---|
| 3,085,336 | 4/1963 | Kesling | 32/14 A |
| 3,178,821 | 4/1965 | Kesling | 32/14 A |
| 3,408,739 | 11/1968 | Johnson | 32/14 A |
| 3,496,637 | 2/1970 | Etengoff | 32/14 A |
| 3,497,954 | 3/1970 | Kesling | 32/14 A |
| 3,765,091 | 10/1973 | Northcutt | 32/14 A |

*Primary Examiner*—Louis G. Mancene
*Assistant Examiner*—Jack Q. Lever
*Attorney, Agent, or Firm*—Bacon & Thomas

[57] ABSTRACT

A bandless orthodontic bracket for a tooth straightening assembly is attachable to the labial or buccal surface of a tooth with a cement. The portion of the bracket adjacent the tooth is provided with at least one undercut recess in which the cement is accommodated so as to provide a "physical" lock between the cement, when set, and the bracket. The frontal portion of the bracket, which is on the reverse side to the labial surface abutting portion, is provided with a smooth bow-shaped channel for accommodating a horizontally disposed arch wire. The arch wire makes contact with the base of the convex channel at one point and permits relative movement with respect to the bracket during mesiodistal tilting of the tooth.

17 Claims, 8 Drawing Figures

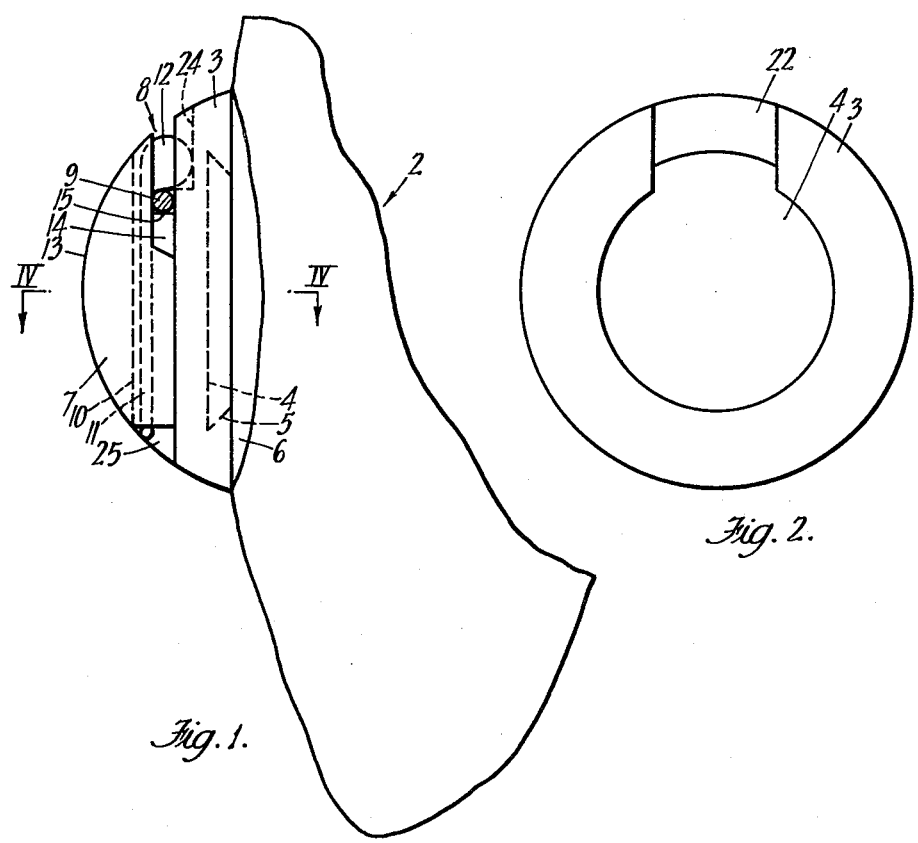
Fig. 1.
Fig. 2.
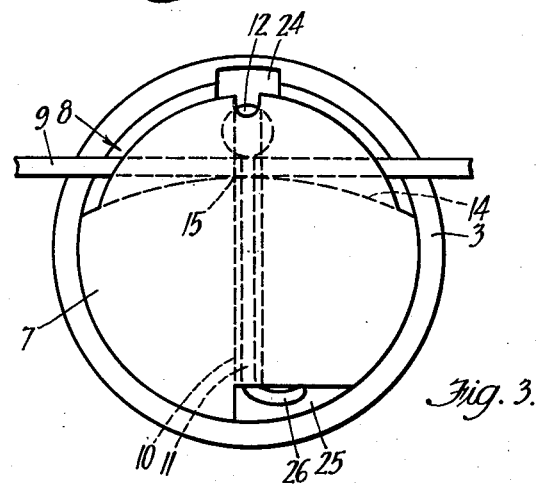
Fig. 3.
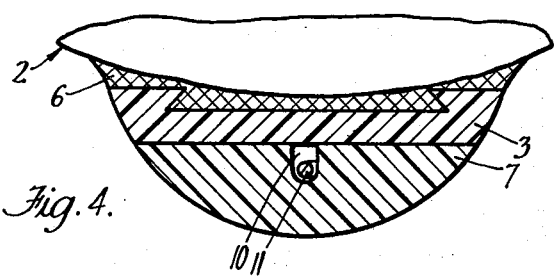
Fig. 4.

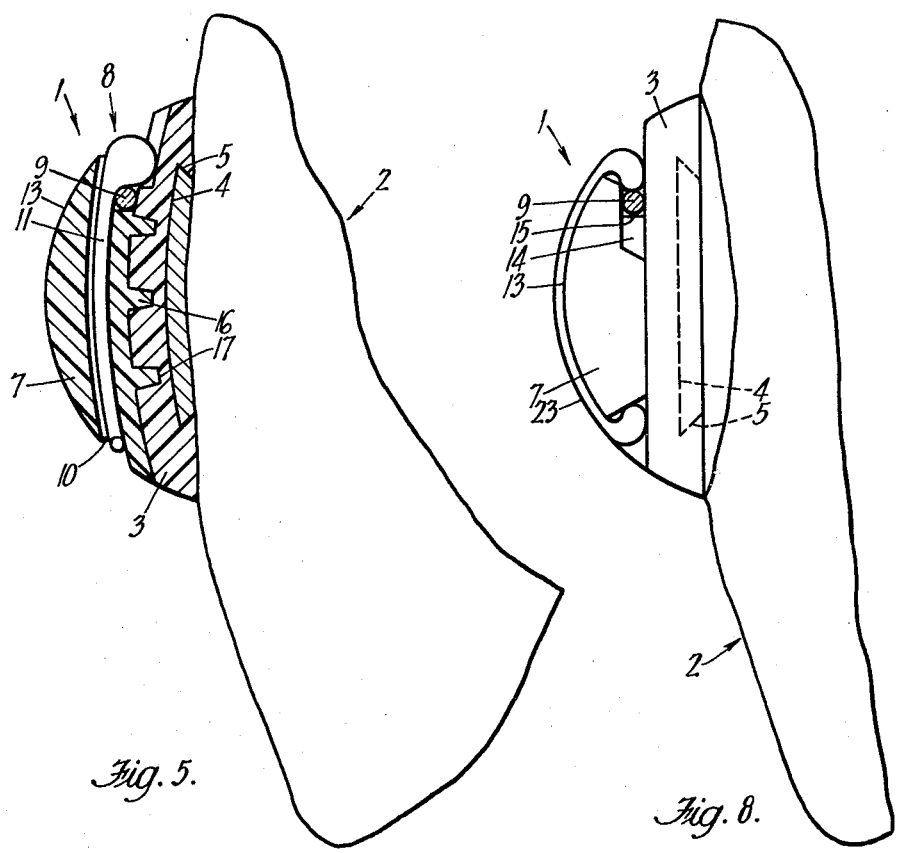
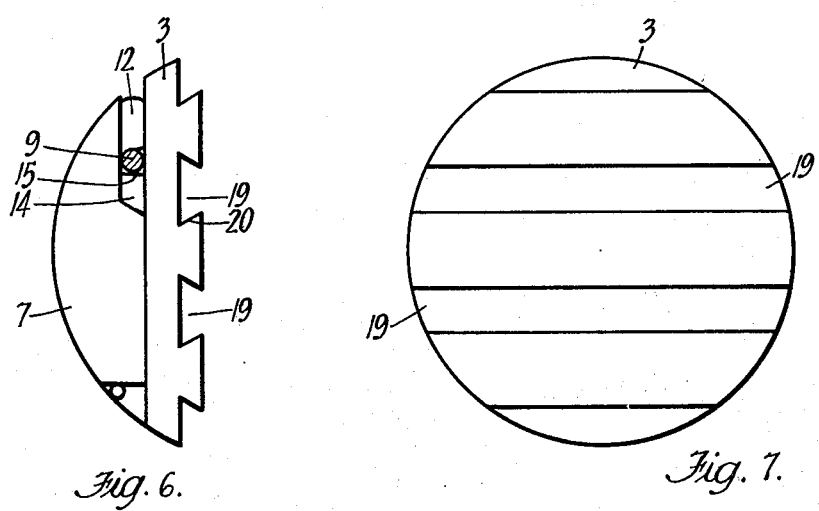

ORTHODONTIC BRACKETS

BACKGROUND OF THE INVENTION

The present invention relates to the field of orthodontics, that is to say, that branch of dentistry concerned with correcting and preventing irregularities of the teeth so as to bring about proper occlusion. Maloccluded teeth may be straightened by the provision of a horizontal arch wire, anchored at each end to suitable anchor teeth, such as molars, and held in a horizontal disposition by means of brackets connected to appropriate teeth. One such well known straightening method is the Begg Light Wire Technique (see "American Journal of Orthodontics," volume 42, No. 7 July 1956 page 48). In this method there is employed an orthodontic bracket formed of metal and comprising base and top portions, with the under surface of the base welded to a band which, in use, embraces the tooth and the top being provided with means — for instance, one or more closable slots — for accommodating the arch wire.

The orthodontic brackets of the Begg type are, however, not particularly suitable for straightening the teeth in a mesiodistal direction (that is, toward and away from the midpoint and endpoints of the dental arch) as there is insufficient provision for the arch wire to pivot in relation to the bracket as the tooth is displaced mesiodistally.

U.S. Pat. No. 3,408,739 filed Apr. 18, 1966 by Frank W. Johnston for "Orthodontic Bracket" attempts to overcome this problem by providing an orthodontic bracket with an integral pivotal edge to support the light arch wire. The bracket includes an occulusalgingivally extending channel to receive a lock pin for securing the light arch wire against the pivotal edge. The pivotal edge of the Johnston bracket provides two single points of contact for the arch wire. This two-point contact has, however, been found in practice to tend to displace the tooth in an occulusalgingival direction and thus the effectiveness of the bracket is considerably reduced.

In practice, however, the pivotal edge on Johnston's bracket tends to weaken the wire at the point of contact therewith so that in prolonged use there is a stretching of the wire and loss of efficiency. Also, there is a tendency for the wire to "catch" on the edge and thus hinder the mesiodistal displacement of the tooth.

It is therefore an object of the present invention to provide an orthodontic bracket which permits mesiodistal tipping of a maloccluded tooth and which does not have the aforementioned disadvantages of the Begg and Johnston brackets.

Orthodontic brackets in common use are attached to the teeth either by metal tooth embracing bands or cement. Tooth embracing bands are cumbersome, less hygienic and have poorer aesthetics in use while cements have the common disadvantage that they are either suitable for specifically adhering to the tooth, or the bracket material, but not both.

It is therefore a further object of the present invention to provide an orthodontic bracket which is usable with cements which are specifically suitable for adhering to teeth only.

SUMMARY OF THE INVENTION

Briefly stated, the orthodontic bracket according to one aspect of the present invention comprises first and second opposed portions, the first portion being adapted for attachment to the labial surface of a tooth and the second or frontal portion being adapted to accommodate a horizontally disposed arch wire; the first portion having one or more undercut recesses for accommodating a cement, and the arrangement and construction being such that, upon cementing of the bracket to the tooth and hardening of the cement, there is a physical lock between the bracket and the hardened cement. This physical lock makes it unnecessary to employ a cement which is adherable to the material of the bracket. A cement may therefore be chosen on the basis of its specific suitability with respect to the tooth enamel, that is, on the basis of good adherability to tooth enamel and removability from the tooth enamel after use.

In a further aspect of the invention, the second portion is provided with a channel for accommodating the arch wire, the base of the channel being bow-shaped in the longitudinal direction of the channel. In use, the arch wire sits in the channel, making contact with the base of the channel. This bow-shaped base permits unimpeded relative movement of the bracket with respect to the horizontal arch wire and thus readily permits mesiodistal tipping of a maloccluded tooth.

BRIEF DESCRIPTION OF THE DRAWINGS

FIG. 1 is a side-elevational view showing a bracket according to the invention fixed to a tooth;

FIG. 2 is an underside view of the bracket illustrated in FIG. 1;

FIG. 3 is a front-elevational view of the bracket illustrated in FIGS. 1 and 2;

FIG. 4 is a cross-sectional view taken along line IV — IV of FIG. 1;

FIG. 5 is a side-on cross-sectional view showing a bracket according to a further modification of the invention, fixed to a tooth;

FIG. 6 is a cross-sectional side view of a modified bracket according to the invention, showing several recesses in its labial surface abutting portion;

FIG. 7 is an underside view of the bracket illustrated in FIG. 6; and

FIG. 8 is a side-elevational view showing a bracket fixed to a tooth according to yet a further modification of the invention.

DESCRIPTION OF THE PREFERRED EMBODIMENTS

Referring to FIGS. 1–4 and particularly to FIG. 1, a bracket, indicated generally by reference numeral 1, is shown attached to the labial surface of a canine tooth. The bracket comprises a first portion 3 having an undercut recess 4. The undercut recess is circular or pear-shaped when seen in the position illustrated in FIG. 2, and has an increasing diameter in the direction away from the tooth 2. The recess accommodates a cement 6 which forms a "physical lock" with the bracket by virtue of the lip 5 preventing the cement, once set, from coming out of the recess. It will be apparent that the provision of such an undercut recess will permit the use of a cement which has specific suitability for adhering to teeth. This is important since, as previously mentioned, cements suitable for adhering to teeth have been found to have by no means the same affinity for brackets. A further obvious advantage is that the same cement can be used no matter what the material of construction of the bracket is; usual bracket materials being metal or plastics, with plastics materials being preferable in view of their greater adaptability.

The recess 4 also takes account of the convexity of some teeth by permitting the tooth to extend into the recess as illustrated in FIG. 4. This natural tooth curvature is not accommodated by conventional brackets which means that for a highly curved tooth it is difficult to satisfactorily secure a bracket thereto.

A spillway 22 (see FIG. 2) is provided in the first portion and communicates the interior of the recess 4 with the exterior of the bracket. This spillway 4 permits excess cement to flow out of the recess 4 as the bracket is adhered to the tooth.

A second or frontal portion 7, on the reverse side of the bracket to the recess 4, is conventional insofar as it includes a narrow channel 8 through with passes an arch wire 9, and an open-topped occulusalgingivally extending bore 10 leading downwards from the midpoint, and just forward of the channel 8 and accommodating the shank of a locking pin 11, the head 12 of which overhangs the arch wire 9 and so prevents inadvertent removal of the arch wire from the channel 8. The head 12 of the locking pin 11 extends into a slot 24 in the first portion 3 of the bracket. The second portion 7 does, however, have three significant distinguishing features. One of these is the rounded or dome-like contour of its upper surface 13.

The conventional bracket top is overall more box-like, with a number of sharp corners. Food tends to catch on these corners and consequently there is a shearing action on the bracket which can ultimately lead to fracture or loosening, if not loss, of the bracket. This problem is virtually non-existent where there are no sharp corners. The rounded shape also provides greater strength at the sides of the bracket, a position at which failure frequently occurs in the more conventionally shaped plastic brackets. The second distinguishing feature is the bow-shaped base 14 of the channel 8 (see FIG. 3 in particular). The conventional bracket top has a flat channel base, and, if there is slight lateral tilting of the tooth, there is a tendency for the arch wire to catch on one end of the channel base. Over a period of time, such contact may weaken the arch wire and/or the bracket itself. The provision of a bow-shaped channel base 14, on the other hand, ensures that the arch wire 9 bears against the curved central portion 15 of the base at all times, even if not at precisely the same point. It also ensures maximum contact of the bracket on the labial aspect of the arch wire and minimum contact on the occlusal aspect of the arch wire. This form of contact gives rise to greater leverage for tipping the tooth mesiodistally and does not contribute to weakening of the wire and/or the bracket. The third distinguishing feature is the presence of a cavity 25 in the lower section of the frontal portion. This cavity is provided so that the tip 26 of the locking pin may be bent at right-angles to its shank and retained firmly in place in the shaft. These three distinguishing features are merely preferred features, and it is to be understood, therefore, that brackets in accordance with the invention may also embody neither feature or simply one of those features.

Referring to FIG. 5 of the drawings, where corresponding reference numerals to those of the previous Figures show corresponding features, there is illustrated a modified bracket wherein the first portion 3 is separable from the frontal portion 7. This is achievable by a "press-stud" arrangement, that is, an arrangement whereby tappered peg-shaped protrusions 16 in the frontal portion 7 press-fit into corresponding depressions 17 in the surface of the first portion 3. This arrangement enables rotational adjustment of the second portion 7 relative to the first portion 3.

FIGS. 6 and 7 illustrate a bracket which differs from the FIG. 1 embodiment in that there are several recesses 19 rather than one recess in the first portion 3. Each recess 19 is undercut similarly to the recess 4 of FIG. 1 and has two mutually opposed lips 20 which prevent the cement, once it has set, from coming out of the recess. A "physical-lock" is thus formed in a similar manner to that described in connexion with FIG. 1.

FIG. 8 illustrates yet a further embodiment of the invention, thus time in the form of a bracket assembly, in which a generally C-shaped snap-on locking pin 23 is used in place of the pin 11 of FIG. 1. No vertical bore is required for the snap-on pin, although it may be desirable to incorporate a vertical locating slot in the domed surface of the top so as to prevent slewing of the pin away from a vertical plane which is generally at right angles to the arch wire 9.

It is to be understood that the construction particularly described is merely a preferred embodiment of this invention and that variations and modifications may be made to that construction without departing from the spirit and scope of this invention which includes every novel feature and combination of features herein disclosed.

I claim:

1. An orthodontic bracket comprising first and second opposed portions, the first portion being adapted for attachment to the labial surface of a tooth and the second portion being adapted to accommodate a horizontally disposed arch wire; the first portion having at least one undercut recess for accommodating a cement, and the arrangement and construction being such that, upon cementing of the bracket to the tooth and hardening of the cement, there is a physical lock between the bracket and the hardened cement said first and second portions being separable and being connected by tappered peg-shaped protrusions which press-fit into corresponding depressions in the surface of the first portion.

2. An orthodontic bracket according to claim 1 in which the undercut recess increases in dimension in a direction away from the labial surface contacting portion of the bracket.

3. An orthodontic bracket according to claim 2 in which there is a single undercut recess comprising a substantially circular depression in the labial surface contacting portion of the bracket.

4. An orthodontic bracket according to claim 1 wherein there is a single recess in the labial surface contacting portion of the bracket, said recess being provided with a spillway through which excess cement may flow when the bracket is being adhered to the tooth.

5. An orthodontic bracket according to claim 1 wherein the second portion is domed-shaped and the first portion is generally frusto-conical shaped.

6. An orthodontic bracket according to claim 1 wherein a bore extends occulusalgingivally through the second portion of the bracket and accommodates a locking pin, the head of which overhangs and locks the arch wire when in position on the tooth.

7. An orthodontic bracket comprising first and second opposed portions, the first portion being adapted for attachment to the labial surface of a tooth and the second portion being adapted to accommodate a horizontally disposed arch wire; the second portion being provided with a channel for accommodating the arch wire, and the base of the channel being bow-shaped in the longitudinal direction of the channel providing along its length a continuous, convex support surface for the arch wire to permit substantially unimpeded relative movement of the bracket with respect to the arch wire.

8. An orthodontic bracket according to claim 7 wherein the second portion is dome-shaped and the first portion is generally frusto-conical shaped.

9. An orthodontic bracket according to claim 8 wherein a bore extends occulusalgingivally through the second portion of the bracket and accommodates a locking pin, the head of which overhangs and locks the arch wire within the channel.

10. An orthodontic bracket comprising first and second opposed portions, the first portion being adapted for attachment to the labial surface of a tooth and the second portion being adapted to accommodate a horizontally disposed arch wire in a horizontal channel provided therein; the first portion characterized by having at least one undercut recess for accommodating a cement, and the base of the channel in the second portion characterized by being bow-shaped in the longitudinal direction of the channel providing along its length a continuous convex support surface for the arch wire, the construction and arrangement being such that, upon cementing of the bracket to the tooth and hardening of the cement, there is a physical lock between the bracket and the hardened cement and the convex support surface for the arch wire permits substantially unimpeded relative movement of the bracket with respect to the arch wire.

11. An orthodontic bracket as claimed in claim 10 in which the undercut recess increases in dimension in a direction away from the labial surface contacting portion of the bracket.

12. An orthodontic bracket according to claim 11 in which there is a single undercut recess comprising a substantially circular depression in the labial surface contacting portion of the bracket.

13. An orthodontic bracket according to claim 11 in which there are a plurality of longitudinally parallel recesses in the labial surface contacting portion of the bracket.

14. An orthodontic bracket according to claim 10 wherein there is a single recess in the labial surface contacting portion of the bracket, said recess being provided with a spillway through which excess cement may flow when the bracket is being adhered to the tooth.

15. An orthodontic bracket according to claim 10 wherein the second portion is domed-shaped and the first portion is generally frusto-conical shaped.

16. An orthodontic bracket according to claim 10 wherein a bore extends occulusalgingivally through the second portion of the bracket and accommodates a locking pin, the head of which overhangs and locks the arch wire when in position on the tooth.

17. An orthodontic bracket according to claim 16 wherein the second portion of the bracket has a cavity into which the tip of the locking pin is bent.

* * * * *